US006803482B2

United States Patent
Jenne et al.

(10) Patent No.: US 6,803,482 B2
(45) Date of Patent: Oct. 12, 2004

(54) PROCESS FOR THE PRODUCTION OF ISOCYANATES IN THE GAS PHASE

(75) Inventors: Marc Jenne, Köln (DE); Heiko Herold, Neuss (DE); Martin Friedrich, Köln (DE); Herbert Stutz, Dormagen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/437,509

(22) Filed: May 14, 2003

(65) Prior Publication Data

US 2003/0216597 A1 Nov. 20, 2003

(30) Foreign Application Priority Data

May 17, 2002 (DE) .......................................... 102 22 023

(51) Int. Cl.⁷ ............................................. C07C 118/00
(52) U.S. Cl. ....................................................... 560/347
(58) Field of Search .......................................... 560/347

(56) References Cited

U.S. PATENT DOCUMENTS

| 4,847,408 A | 7/1989 | Frosch et al. ................ 289/347 |
| 5,391,683 A | 2/1995 | Joulak et al. ................. 528/67 |
| 5,449,818 A | 9/1995 | Biskup et al. .............. 570/347 |

Primary Examiner—Paul J. Killos
(74) Attorney, Agent, or Firm—Joseph C. Gil; Lyndanne M. Whalen

(57) ABSTRACT

Isocyanates are produced in the gas phase in a manner such that temperature fluctuations over time and temperature distribution asymmetry are prevented. In this improved process, performance of the reaction in tubular reactors is accomplished by flow-related measures such as homogenization and centering of the educt streams. The formation of polymeric secondary products, which result in baked-on deposits in the reactor and a reduction in reactor service life, is consequently prevented.

9 Claims, 1 Drawing Sheet

PROCESS FOR THE PRODUCTION OF ISOCYANATES IN THE GAS PHASE

BACKGROUND OF THE INVENTION

The present invention relates to a process for the production of isocyanates in the gas phase in which temperature fluctuations over time and temperature distribution asymmetry are prevented. This is achieved by improved performance of the reaction in tubular reactors by flow-related measures such as homogenization and centering of the educt streams. The formation of polymeric secondary products, which result in baked-on deposits in the reactor and a reduction in reactor service life, is consequently prevented.

EP-A 0 289 840 describes a process for the production of (cyclo)aliphatic diisocyanates by phosgenation of the corresponding, vaporous (cyclo)aliphatic diamines at 200° C. to 600° C. Phosgene is supplied in stoichiometric excess. The superheated streams of vaporous (cyclo)aliphatic diamine or (cyclo)aliphatic diamine/inert gas mixture on the one hand and of phosgene on the other hand are passed continuously into a cylindrical reaction chamber, where they are mixed together and caused to react. The exothermic phosgenation reaction is performed while maintaining a turbulent flow.

Gaseous educts are frequently reacted in tubular reactors. If the jet mixer principle is applied (Chemie-Ing.-Techn. 44 (1972), p. 1055, FIG. 10), two educt streams, A and B are supplied to the tubular reactor. Educt stream A is supplied via a central nozzle and educt stream B via an annular space between central nozzle and tubular reactor wall. The flow velocity of the educt stream A is high relative to the flow velocity of educt stream B. This causes intensive mixing of and consequently reaction of the reaction partners in the tubular reactor. This method of performing the reaction has become industrially significant in the production of aromatic diisocyanates by phosgenation of aromatic diamines in the gas phase (e.g. EP-A 0 570 799).

However, the known processes exhibit major temperature fluctuations of up to 50° C. during performance of the reaction. Moreover, temperature distribution asymmetry of up to 100° C. may be measured in the circumferential direction of the cylindrical reaction chamber or of the tubular reactor, e.g. using thermocouples.

A consequence of the temperature fluctuations and temperature distribution asymmetries is the formation of polymeric secondary products, which result in baked-on deposits and blockages in the reactor and thus in a reduction in the service life of the reactors.

SUMMARY OF THE INVENTION

The object of the invention is therefore to provide a process for the production of (cyclo)aliphatic and aromatic diisocyanates by phosgenation of corresponding (cyclo) aliphatic and aromatic diamines in the gas phase at high temperatures, in which process the temperature fluctuations in the reaction zone and the temperature distribution asymmetries are prevented to the greatest possible extent.

It has now surprisingly been found that homogenization of the educt stream B supplied via the annular space of the tubular reactor and maximally central supply of the two educt streams A and B into the tubular reactor have a marked positive influence on the stability of the reaction zone and thus on the gas phase reaction overall. As a consequence of performing the reaction in a more stable-manner, the observed temperature fluctuations diminish markedly, and the temperature distribution asymmetry disappears virtually completely. Thus, the disadvantages of the prior art process may be markedly reduced, by subjecting the educt streams to the measures according to the inventions described below in more detail.

BRIEF DESCRIPTION OF THE DRAWING

The FIGURE illustrates a tubular reactor suitable for use in the practice of the present invention.

DETAILED DESCRIPTION OF THE INVENTION

Figure 1:
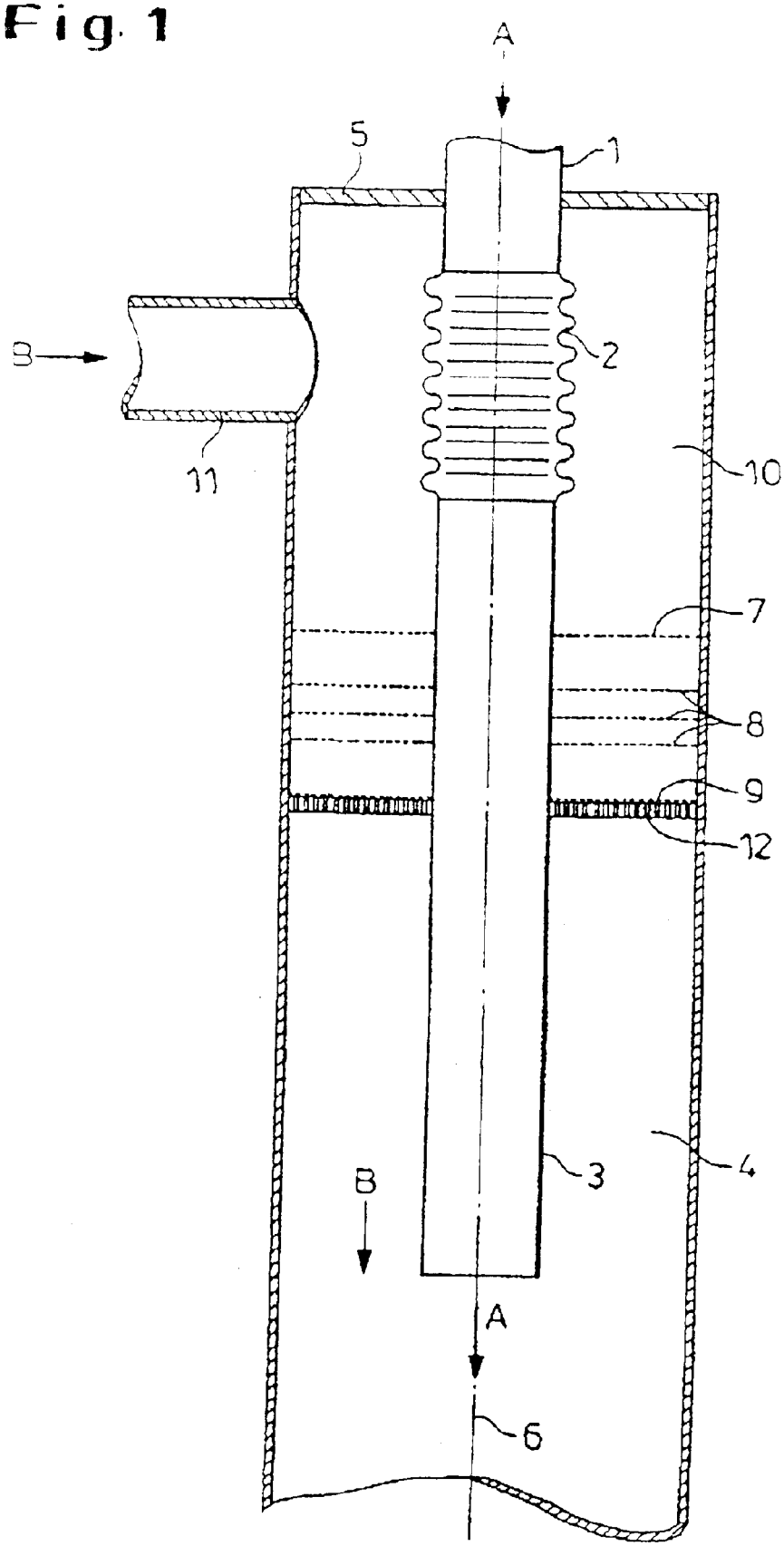

The present invention provides a process for the production of diisocyanates and triisocyanates of the general formula (I)

$$R(NCO)_n \qquad (I),$$

in which

R represents a (cyclo)aliphatic or aromatic hydrocarbon residue with up to 15 carbon atoms, preferably 4 to 13 carbon atoms, with the proviso that at least 2 carbon atoms are arranged between two NCO groups and n represents the number 2 or 3, by phosgenation of the corresponding diamines and/or triamines of the general formula (II) in the gas phase

$$R(NH_2)_n \qquad (II),$$

in which

R represents a (cyclo)aliphatic or aromatic hydrocarbon residue with up to 15, preferably 4 to 13 carbon atoms, with the proviso that at least two carbon atoms are arranged between two amino groups and n represents the number 2 or 3.

The phosgenation is performed in a tubular reactor which includes a central nozzle and an annular space between the central nozzle and the wall of the tubular reactor. The central nozzle is centered in the tubular reactor by at least two flow homogenizers arranged in the annular space. The central nozzle is connected with an inlet for one of the educt streams via a flexible connecting tube and the inlet for a second educt stream is arranged in the annular space. The educt stream containing the diamine(s) and/or triamine(s) is supplied to the tubular reactor via the central nozzle. The educt stream containing phosgene is supplied to the tubular reactor via the annular space and the velocity of the flow in the annular space is homogenized with the flow homogenizers over the entire cross-section of the annular space.

In an alternative embodiment of the process according to the invention, the educt stream containing the diamine(s) and/or triamine(s) and the educt stream containing phosgene are switched, such that the educt stream containing the diamine(s) and/or triamine(s) is supplied to the tubular reactor via the annular space and the educt stream containing phosgene is supplied to the tubular reactor via the central nozzle.

According to the invention, it is preferred that the second flow homogenizer or, if there are more than two flow homogenizers, the last flow homogenizer before the educt stream B enters the tubular reactor be provided as a combined unit. This combined unit is composed of a flow homogenizer and a flow equalizer.

The task of the flow homogenizer(s) is to homogenize the flow velocity of the educt stream apportioned into the annular space over the entire cross-section of the annular space. Known flow homogenizers are, inter alia, perforated plates, screens, sintered metal, fritted elements or beds. Perforated plates are preferably used.

The task of the flow equalizer is to orient the flow axially, i.e. oblique flow and swirl are prevented. Known flow equalizers are, inter alia, honeycomb structures and tubular structures.

Hoses and preferably compensators (corrugated hoses made, for example, of stainless steel) are suitable as flexible connecting tubes.

The process according to the invention allows the local flow velocity to deviate by at most ±10%, preferably ±2%, from the flow velocity, averaged over the total cross-section, of the educt stream apportioned via the annular space.

In the process according to the invention, diisocyanate(s) and/or triisocyanate(s) are produced from the corresponding diamine(s) and/or triamine(s).

Diisocyanates are preferably produced in the process according to the invention by phosgenation of the corresponding diamines.

In the process according to the invention, 1,8-diisocyanato-4-(isocyanatomethyl)octane, triisocyanatononane (TIN), is preferably produced as the triisocyanate represented by the formula (I).

Typical examples of suitable aliphatic diamines are given, for example, in EP-A 0 289 840, and typical examples of suitable aliphatic triamines are given, for example, in EP-A 749 958. These diamines are suitable for producing the corresponding diisocyanates or triisocyanates by the process according to the invention.

Isophoronediamine (IPDA), hexamethylenediamine (HDA) and bis(p-aminocyclohexyl)methane are particularly preferred.

Typical examples of suitable aromatic diamines are the pure isomers or the isomer mixtures of diaminobenzene, diaminotoluene, diaminodimethylbenzene, diaminonaphthalene and of diaminodiphenylmethane. 2,4/2,6-toluenediamine mixtures of 80/20 and 65/35 isomer ratios or the pure 2,4-toluenediamine isomer are preferred.

The triamine preferably used is 1,8-diamino-4-(aminomethyl)octane, triaminononane.

The starting amines of the formula (II) are supplied in gaseous form to the reactor and, before the process according to the invention is performed, optionally vaporized and heated preferably to 200° C. to 600° C., more preferably to 250° C. to 450° C., and, optionally diluted with an inert gas such as $N_2$, Ne, He, Ar or with the vapors of an inert solvent, fed into the reactor. The phosgene is supplied to the tubular reactor in stoichiometric excess and at 200° C. to 600° C. If one or more aliphatic diamines are used, the molar phosgene excess preferably amounts to between 25% and 250% relative to an amino group, while it preferably amounts to between 50% and 350% if one or more aliphatic triamines are used. If aromatic diamines are used, the molar phosgene excess preferably amounts to between 150% and 300% relative to an amino group.

The invention is explained below by way of example with reference to the FIGURE. The educt stream A (diamine and/or triamine) flows through the inlet 1, the flexible connecting tube 2 and the central nozzle 3 into the tubular reactor 4. The inlet 1 for the educt stream A is connected rigidly with the lid 5 of the tubular reactor 4. The central nozzle 3 is connected movably with the inlet 1 for the educt stream A via the flexible connecting tube 2.

The central nozzle 3 is held firmly in position by a plurality of flow homogenizers 7, 8 and 9 and is centered with regard to the axis of rotation 6 of the tubular reactor 4. To this end, at least two flow homogenizers 7 and 9 are required, all further flow homogenizer(s) 8 being optional. The flow homogenizers 7, 8 and 9 are built fixedly into the annular space 10 of the tubular reactor and extend over the entire flowed-through cross-section of the annular space.

The educt stream B (phosgene) flows through the inlet 11 into the annular space 10 of the tubular reactor 4. The velocity of the educt stream B is homogenized during passage through the flow homogenizers 7, 8 and 9, resulting in homogenized flow over the entire flowed-through cross-section of the annular space 10. A flow equalizer 12 is arranged directly downstream of the last flow homogenizer 9 in the flow direction.

This additionally effects axial orientation of the flow velocity of the educt stream B in the direction of the axis of rotation 6.

The invention is further illustrated but is not intended to be limited by the following examples in which all parts and percentages are by weight unless otherwise specified.

EXAMPLE

A hexamethylenediamine (HDA)/inert gas mixture is fed continuously to a tubular reactor of the type shown in the FIGURE as educt stream A and phosgene as educt stream B. Both educt streams were at a temperature of 300 degrees Celsius.

Testing was performed on the one hand in accordance with the invention with a tubular reactor such as that shown in the FIGURE, which had two flow homogenizers 7 and 9. The flow homogenizer(s) 8 and the flow equalizer 12 were not present in the tubular reactor 4 used in testing according to the invention.

On the other hand, testing was performed as a comparative example using a tubular reactor which contains packing instead of the flow homogenizers 7 and 9, which packing was intended to ensure homogenization and centering of the educt streams. The flexible connecting tube 2 was replaced by a rigid connection of the central nozzle 3 with the inlet 1 of the tubular reactor 4.

At three measurement planes positioned downstream of the central nozzle 3, the temperature was measured at the cylindrical outer wall of the tubular reactor 4 by means of thermocouples. Three thermocouples were attached to the outer wall at each measurement plane, spaced in a circle therearound at 120° intervals.

In the process performed as a comparative example, temperature fluctuations over time of up to 50° C. occurred at the measurement points. Moreover, temperature distribution asymmetry of up to 100° C. arose in the circumferential direction. With the process performed according to the invention, the temperature fluctuations over time were reduced markedly to approx. 10° C., while the asymmetries disappeared completely. The formation of polymeric secondary products, which deposited on the wall of the tubular reactor, was thus reduced, leading to a marked extension of reactor service life.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of a diisocyanate and/or triisocyanate represented by the general formula (I)

$$R(NCO)_n \qquad (I),$$

in which
R represents a (cyclo)aliphatic or aromatic hydrocarbon residue with 2 to 15 carbon atoms, provided that at least 2 carbon atoms are arranged between two NCO groups and
n represents 2 or 3,
comprising phosgenating a corresponding diamine and/or triamine represented by the general formula (II)

$$R(NH_2)_n \qquad (II),$$

in the gas phase in a tubular reactor which further comprises
(a) a central nozzle which is centered in the tubular reactor by
(b) at least two flow homogenizers arranged in
(c) an annular space between the central nozzle and
(d) a wall of the tubular reactor,
(e) a flexible connecting tube which connects the central nozzle with
(f) a first inlet for a first educt stream,
(g) a second inlet for a second educt stream which is arranged in the annular space
in a manner such that
(1) the first educt stream is supplied to the tubular reactor via the central nozzle,
(2) the second educt stream is supplied to the tubular reactor via the annular space, and
(3) velocity of flow in the annular space is homogenized with the flow homogenizers over the entire cross-section of the annular space.

2. The process of claim 1 in which the first educt stream contains a diamine and/or triamine and the second educt stream contains phosgene.

3. The process of claim 1 in which the first educt stream contains phosgene and the second educt stream contains a diamine and/or triamine.

4. The process of claim 1 in which a diamine is phosgenated to produce a diisocyanate.

5. The process of claim 1 in which vaporous diamine is supplied to the tubular reactor at 200° C. to 600° C. via the central nozzle and phosgene is supplied to the tubular reactor in stoichiometric excess at 200° C. to 600° C. via the annular space.

6. The process of claim 1 in which isophoronediamine (IPDA), hexamethylenediamine (HDA) or bis(p-aminocyclohexyl)methane is phosgenated.

7. The process of claim 1 in which an isomeric mixture of 2,4/2,6-toluenediamine or pure 2,4-toluenediamine is phosgenated.

8. The process of claim 1 in which triisocyanatononane is the product produced.

9. The process of claim 1 in which R represents an aliphatic, cycloaliphatic or aromatic hydrocarbon residue having from 4 to 13 carbon atoms.

* * * * *